United States Patent [19]

May

[11] 4,145,766

[45] Mar. 27, 1979

[54] ADJUSTABLE FRICTION JOINT FOR AN ARTIFICIAL KNEE

[75] Inventor: Denis R. W. May, London, England

[73] Assignee: J. E. Hanger & Company Limited, London, England

[21] Appl. No.: 859,893

[22] Filed: Dec. 12, 1977

[30] Foreign Application Priority Data

Dec. 15, 1976 [GB] United Kingdom ............... 52287/76

[51] Int. Cl.² ............................................. A61F 1/08
[52] U.S. Cl. ............................................. 3/28; 3/22
[58] Field of Search ........................... 3/28, 26, 22, 27

[56] References Cited

U.S. PATENT DOCUMENTS 2,590,782  3/1952  Mayack ................................. 3/22 X
2,667,644  2/1954  Johnson ................................ 3/27 X

FOREIGN PATENT DOCUMENTS 2332993  1/1975  Fed. Rep. of Germany ............... 3/22
 810752  1/1937  France ........................................ 3/22

Primary Examiner—Clifford D. Crowder
Attorney, Agent, or Firm—Pollock, VandeSande and Priddy

[57] ABSTRACT

The angular movement of a knee joint of the kind comprising a four bar linkage is controlled by the frictional engagement of a shaft, pivoted at one end to one of the links, with a pivotable plastics bush located between the ends of another link. The plastics bush may be tightened around the shaft to adjust the frictional restraint on the movement of the joint.

5 Claims, 3 Drawing Figures

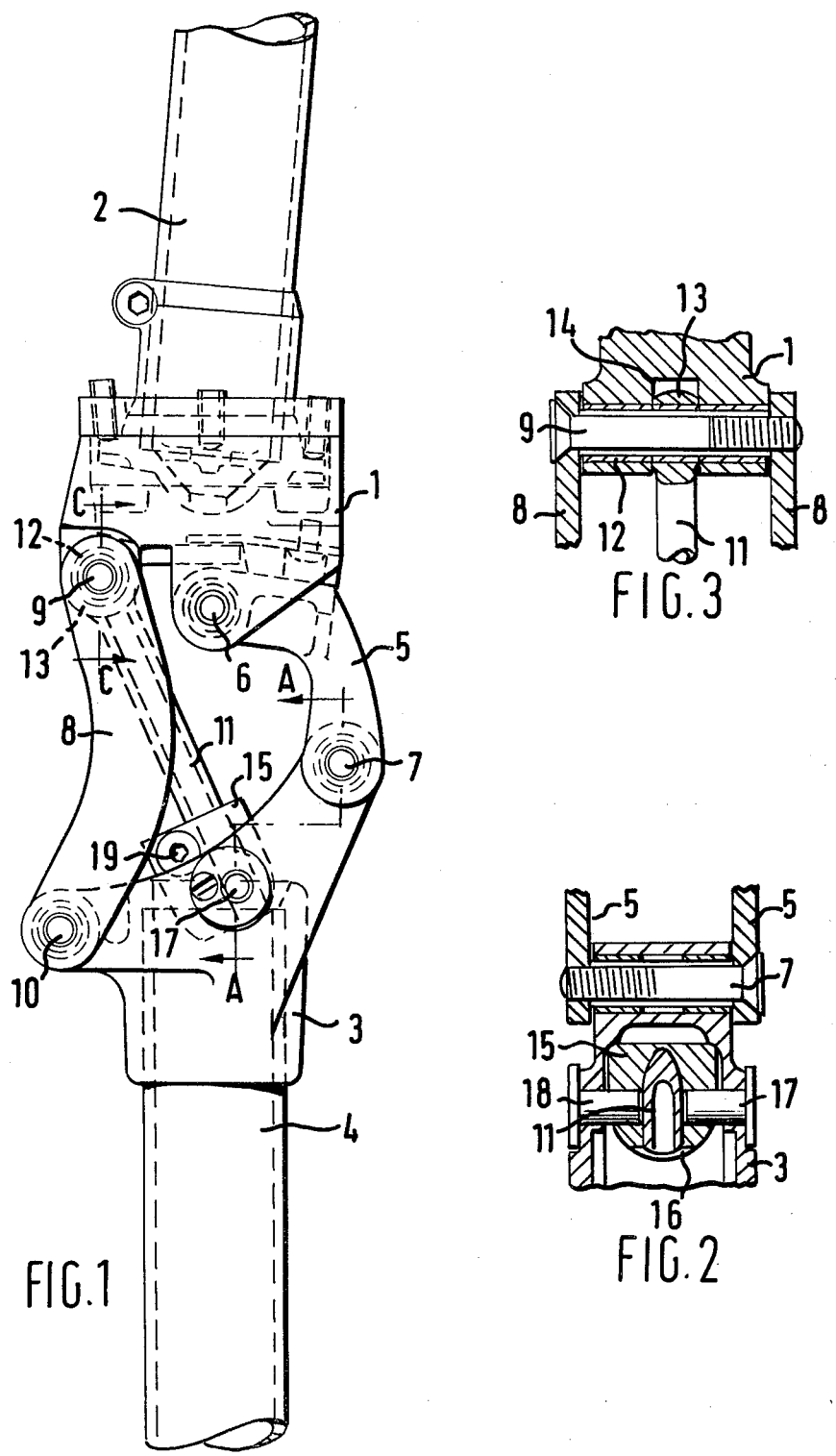

ADJUSTABLE FRICTION JOINT FOR AN ARTIFICIAL KNEE

BACKGROUND OF THE INVENTION

This invention is concerned with artificial legs and more particularly with the knee joints of such legs.

A known type of knee joint comprises a four-bar linkage, two of the links being adapted for conection to a shin portion and a thigh portion respectively and being connected by the other two links. The linkage may be designed so that in bending the knee, there is an initial resistance to angular movement over a predetermined angle followed by substantially free movement to the fully bent position.

An object of the present invention is to control the angular movement of a knee joint of this kind by introducing a frictional restraint on the movement of the links.

PRIOR ART

The most relevant prior art known to the Applicant in U.S. Pat. No. 3,823,424.

SUMMARY OF THE INVENTION

From one aspect, the invention provides a knee joint of the kind referred to including a shaft pivotally connected at one end to one of the links of the four-bar linkage and slidable through a plastics bush pivoted to another link of said linkage. Preferably the shaft is pivotable to the bar formed by the thigh portion and slides through a bush pivoted to the shin portion which forms the other bar.

From another aspect, the invention provides a knee joint of the kind referred to having a shaft pivoted at one end about the pivotal axis connecting two bars of the linkage and slidable through a plastics bush pivotable about an axis situated between the ends of another bar of the linkage.

The plastics bush may have a longitudinal slot and may be tightened around the shaft to control the friction therewith by a screw passing transversely of the slot.

BRIEF DESCRIPTION OF THE DRAWINGS

FIG. 1 is a side view of one embodiment of the invention;

FIG. 2 is a section on the line A—A of FIG. 1; and

FIG. 3 is a section on the line C—C of FIG. 1.

DESCRIPTION OF A PREFERRED FORM

Referring to the drawings, a knee joint comrises a thigh part 1 adapted for connection to a member 2 forming the thigh of the artificial leg, and a shin part 3 adapted for connection to a member 4 forming the shin of the leg. The thigh part 1 and the shin part 3 are pivotally connected to opposite ends of a front link 5 by pivots 6, 7 respectively and to opposite ends of a rear link 8 by pivots 9, 10 respectively. The thigh part 1, front link 5, shin part 3 and rear link 8 form a four-bar chain which may be designed so that there is an initial resistance to relative movement of the thigh and shin over a small angle followed by substantially free movement until the leg is fully bent.

A shaft 11 is pivotably mounted at one end about the axis of the pivot 9 connecting the upper end of the rear link 8 with the thigh part 1. A tube 12 coaxial with the pivot 9 is mounted in the thigh part 1 and passes through a hole in the enlarged end 13 of the shaft 11, the thigh part having a recess 14 to accommodate the end 13.

The other end of the shaft 11 passes through a plastics bush 15 and is a slidable fit therein. This bush 15 is pivotably mounted on the shin part 3 midway between the pivotal connections 7, 10 of the front and rear links 5, 8. A cylindrical recess 16 to receive the bush 15 is formed in the top of the shin part 3 and pins 17, 18 project into this recess to form bearings for the bush 15. The inner ends of the pins 17, 18 are spaced apart to allow passage between them of the shaft 11.

The bush 15 is split longitudinally on one side and a screw 19 connects the portions of the bush on opposite sides of the split. The screw 19 may be threaded in or out to tighten or loosen the bush around the shaft 11 and thereby increase the friction between them.

It will be seen that as the knee joint is bent, the shaft 11 slides through the bush 15 against the frictional force therebetween so that the movement of the joint is controlled. Adjustment of the controlling force is afforded by tightening the bush around the shaft.

It will be understood that the invention is not restricted to the details of the preferred form described by way of example which may be modified without departure from the scope of the accompanying claims.

I claim:

1. In a knee joint comprising a four-bar linkage of which two links are connected to a shin portion and a thigh portion respectively, said shin and thigh portions forming the other two links, the improvement comprising a shaft pivotally connected at one end to one link of said four-bar linkage, and a plastics bush pivoted to another link of said four-bar linkage, said shaft passing through said plastics bush in frictional engagement therewith whereby angular movement of the knee joint is controlled.

2. A knee joint comprising a thigh portion, a shin portion, a front link pivotably connected to the thigh and shin portions and a rear link pivotably connected to the thigh and shin portions and completing a four-bar linkage, a shaft pivoted at one end about the pivotal axis connecting two links of said four-bar linkage and a plastics bush pivotable about an axis located between the ends of another bar of said linkage, said shaft passing through and frictionally engaging said plastics bush.

3. A knee joint as described in claim 2, wherein said shaft is pivotable about the axis of the pivotal connection between said rear link and said thigh portion and said plastics bush is pivoted to said shin portion between said front and rear links.

4. A knee joint as described in claim 2, including means for adjusting the frictional engagement of said plastics bush with said shaft.

5. A knee joint as described in claim 4, wherein said means comprises a screw traversing a longitudinal slot in said bush and threadable into said bush to very the tightness of said bush on said shaft.

* * * * *